(12) United States Patent
Baust et al.

(10) Patent No.: US 8,551,081 B2
(45) Date of Patent: *Oct. 8, 2013

(54) CRYOGENIC SYSTEM

(75) Inventors: John G. Baust, Candor, NY (US); Roy Cheeks, Harpers Ferry, NY (US)

(73) Assignee: Endocare, Inc., Austin, TX (US)

( * ) Notice: Subject to any disclaimer, the term of this patent is extended or adjusted under 35 U.S.C. 154(b) by 57 days.

This patent is subject to a terminal disclaimer.

(21) Appl. No.: 12/896,891

(22) Filed: Oct. 3, 2010

(65) Prior Publication Data

US 2011/0245823 A1    Oct. 6, 2011

Related U.S. Application Data

(63) Continuation of application No. 12/193,949, filed on Aug. 19, 2008, now abandoned, which is a continuation of application No. 11/688,007, filed on Mar. 19, 2007, now Pat. No. 7,416,548, which is a continuation of application No. 10/478,937, filed as application No. PCT/US02/17104 on May 31, 2002, now Pat. No. 7,192,246.

(60) Provisional application No. 60/294,256, filed on May 31, 2001.

(51) Int. Cl.
*A61B 18/02* (2006.01)
*F17C 13/00* (2006.01)

(52) U.S. Cl.
USPC ............... 606/20; 606/21; 606/22; 606/25; 62/50.6

(58) Field of Classification Search
USPC .................. 606/20–22, 25; 62/50.6
See application file for complete search history.

(56) References Cited

U.S. PATENT DOCUMENTS

| | | | |
|---|---|---|---|
| 3,613,689 A | 10/1971 | Crump | |
| 4,345,598 A | 8/1982 | Zobac | |
| 4,367,743 A * | 1/1983 | Gregory | 606/22 |
| 4,376,376 A * | 3/1983 | Gregory | 62/48.1 |
| 4,472,946 A | 9/1984 | Zwick | |
| 4,499,737 A * | 2/1985 | Binnig et al. | 62/56 |
| 4,838,034 A * | 6/1989 | Leonard et al. | 62/50.2 |
| 4,860,545 A * | 8/1989 | Zwick et al. | 62/50.6 |

(Continued)

FOREIGN PATENT DOCUMENTS

WO    02/096270    12/2002

OTHER PUBLICATIONS

International Application No. PCT/US02/17104 International Search Report Dated Dec. 26, 2002 Relative to Corresponding International Publication No. WO 02/096270 Dated Dec. 5, 2002 (3 Pages).

*Primary Examiner* — Lee S Cohen
(74) *Attorney, Agent, or Firm* — Lawrence N. Ginsberg

(57) ABSTRACT

A cryosurgical system and method for supplying cryogen to a probe. The system including a container filled with cryogen and having bellows of a pump submerged within said cryogen. Conduits fluidly interconnect the bellows and a probe that is outside the container to permit the cryogen to be forced from the bellows to the probe upon activation of pump. A pressure relief valve is fluidly coupled to the conduits and positioned between the bellows and the probe. After initially forcing cryogen to the probe at a pressure that establishes a colligative-based sub-cooling of the liquid cryogen, the pressure relief valve is activated to lower the pressure of the cryogen to a running pressure.

21 Claims, 5 Drawing Sheets

(56) References Cited

U.S. PATENT DOCUMENTS

| | | |
|---|---|---|
| 4,946,460 A | 8/1990 | Merry |
| 5,254,116 A | 10/1993 | Baust |
| 5,257,977 A | 11/1993 | Eshel |
| 5,334,181 A | 8/1994 | Rubinsky |
| 5,400,602 A | 3/1995 | Chang |
| 5,573,532 A | 11/1996 | Chang |
| 5,916,212 A | 6/1999 | Baust |
| 5,947,960 A | 9/1999 | Griswold |
| 5,957,963 A * | 9/1999 | Dobak, III ............ 607/104 |
| 6,589,234 B2 | 7/2003 | Lolonde |
| 7,192,426 B2 * | 3/2007 | Baust et al. ............ 606/20 |
| 7,416,548 B2 * | 8/2008 | Baust et al. ............ 606/20 |
| 2009/0043297 A1 | 2/2009 | Baust |

* cited by examiner

CRYOGENIC SYSTEM

CROSS REFERENCE TO RELATED APPLICATIONS

This is a continuation of U.S. application Ser. No. 12/193,949 entitled Cryogenic System, filed Aug. 19, 2008, now abandoned which is a continuation of U.S. application Ser. No. 11/688,007 (now U.S. Pat. No. 7,416,548) entitled Cryogenic System, filed Mar. 19, 2007, which is a continuation of U.S application Ser. No. 10/478,937 (now U.S. Pat. No. 7,192,426) entitled Cryogenic System, filed May 14, 2004, which is the National Stage of International Application No. PCT/US02/17104, filed May 31, 2002, which claims the benefit of U.S. Provisional Application No. 60/294,256, filed on May 31, 2001. The entire contents of U.S. application Ser. Nos. 12/193,949, 11/688,007, 10/478,937, International Application No. PCT/US02/17104 (WO 02/096270), and U.S. application Ser. No. 60/294,256 are incorporated herein by reference thereto.

BACKGROUND OF THE INVENTION

1. Field of the Invention

The present invention relates to a cryogenic system. More specifically, illustrative embodiments of the present invention relate to a cryogenic system for use in cryosurgical procedures.

2. Description of the Related Art

The distribution of boiling (liquid) cryogens, such as liquid nitrogen, is problematic due to the parasitic heat load provided by a cryosurgical device's plumbing or transport circuit, which is maintained at ambient temperature. Pre-cooling the plumbing circuit, even if adequately insulated, causes two-phase flow (liquid-gas mixtures), cryogen boil-off, and choking flow due to gas expansion in the transport circuit. As a result, target temperatures at the distal end of the flow path (i.e., cryoprobe tip) are not reached for many minutes.

Some prior cryogenic systems and devices are disclosed in U.S. Pat. No. 4,345,598 to Zobac et al.; U.S. Pat. No. 4,472,946 to Zwick; U.S. Pat. No. 4,860,545 to Zwick et al.; U.S. Pat. No. 4,946,460 to Merry et al.; U.S. Pat. No. 5,254,116 to Baust et al.; U.S. Pat. No. 5,257,977 to Eshel; U.S. Pat. No. 5,334,181 to Rubinsky et al.; U.S. Pat. No. 5,400,602 to Chang et al.; U.S. Pat. No. 5,573,532 to Chang et al.; and U.S. Pat. No. 5,916,212 to Baust et al., the entire contents of each being hereby incorporated herein by reference thereto, respectively.

SUMMARY OF THE INVENTION

The present invention can be embodied in a cryosurgical system, comprising a container having cryogen within the container; a pump having a piston submerged within the cryogen; a probe outside the container for use in cryosurgical procedures; a system of conduits fluidly interconnecting the piston and the probe permitting the cryogen to be forced from the piston to the probe upon activation of the piston; and a pressure relief device fluidly coupled to the systems of conduits and positioned between the bellows and the probe.

The present invention may also be embodied in a pump assembly for a cryosurgical system, comprising a driving mechanism coupled to an elongated drive shaft; a bellows coupled to the drive shaft and adapted to be submersed in cryogen, the bellows formed from metal; a one-way inlet valve fluidly coupled to the bellows; and a one-way outlet valve fluidly coupled to the bellows.

The present invention may also be embodied in a method of delivering cryogen to a surgical device, comprising providing a container having cryogen within the container; providing a pump having a piston within a cylinder and submerged within the cryogen; providing a surgical instrument outside the container for use in cryosurgical procedures; providing a system of conduits fluidly interconnecting the piston and the surgical instrument permitting the cryogen to be forced from the piston to the probe upon activation of the piston; providing a pressure relief device fluidly coupled to the systems of conduits and positioned between the bellows and the probe; activating the piston to pull cryogen within the cylinder; activating the piston to push the cryogen from the cylinder to the surgical instrument at an initial predetermined pressure.

Other aspects, features, and advantages of the present invention will become apparent from the following detailed description of the illustrated embodiments, the accompanying drawings, and the appended claims.

DETAILED DESCRIPTION OF THE INVENTION

Figure 1:
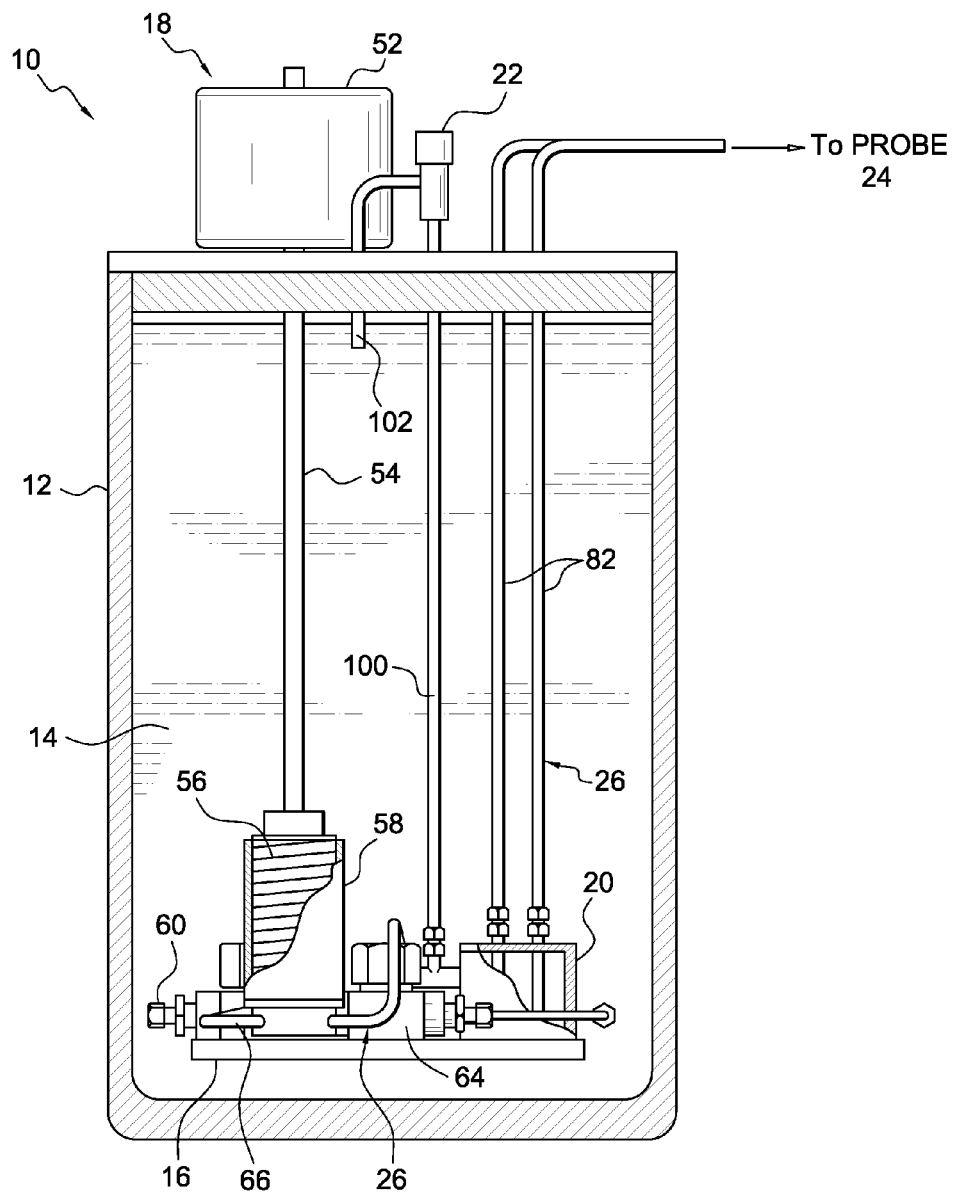
FIG. 1 illustrates a system in accordance with an embodiment of the present invention and includes a cross-sectional view through a container holding cryogen.
Figure 2:
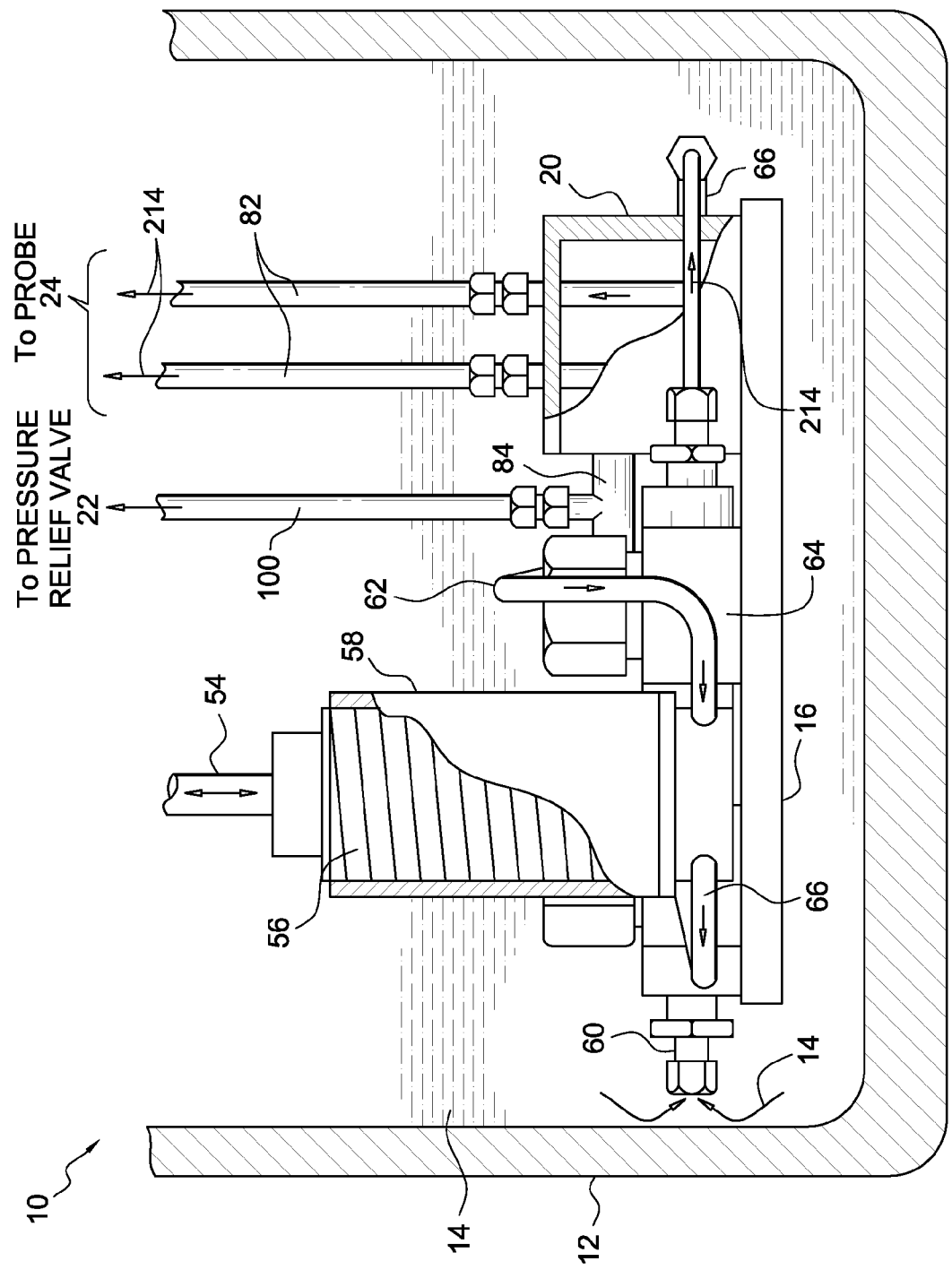
FIG. 2 is an enlarged, elevational view of the container of FIG. 1 and its contents.
Figure 3:
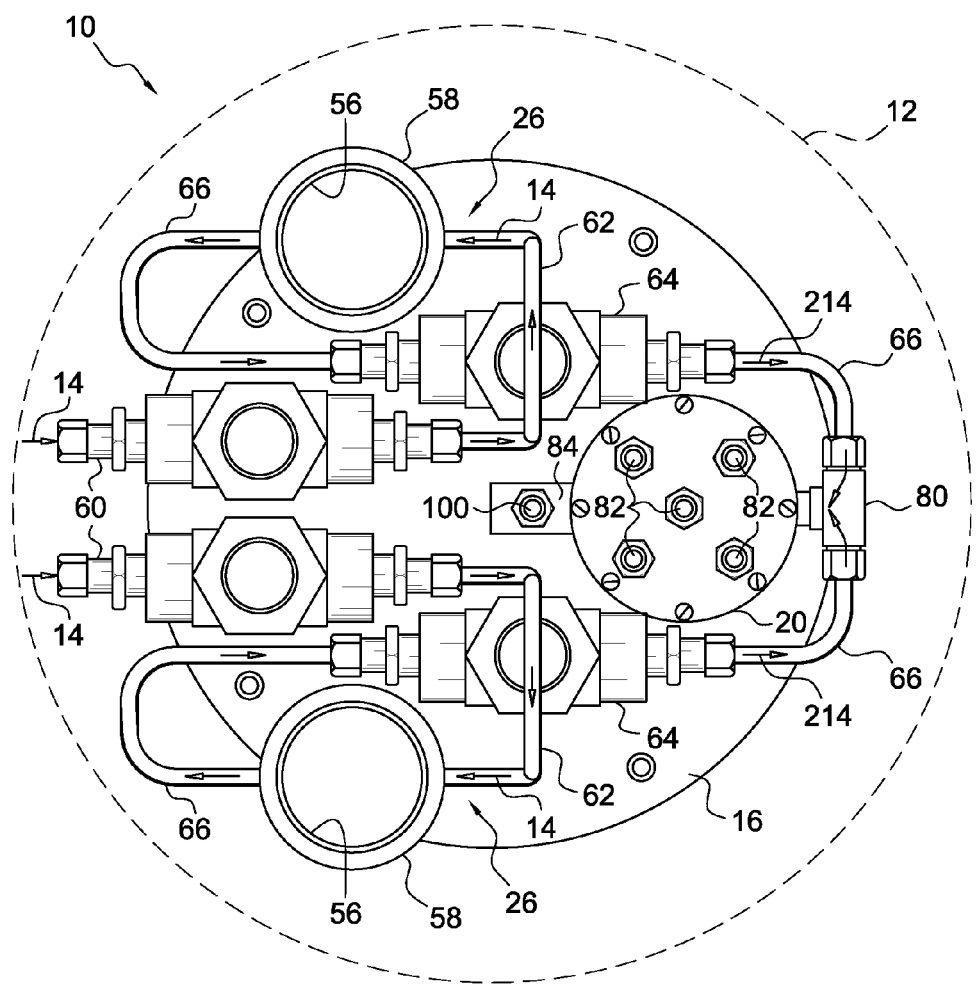
FIG. 3 is an enlarged, top view of the assembly within the container of FIG. 1.
Figure 4:
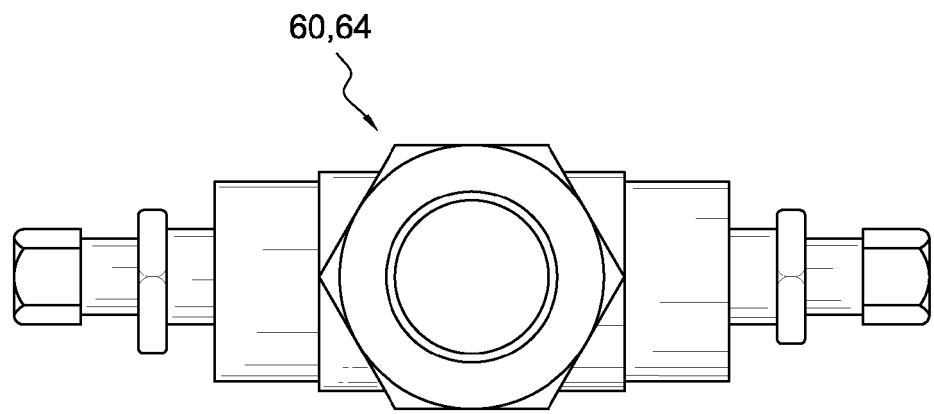
FIG. 4 is a top view of a valve used in the system illustrated in FIGS. 1-3.
Figure 5:
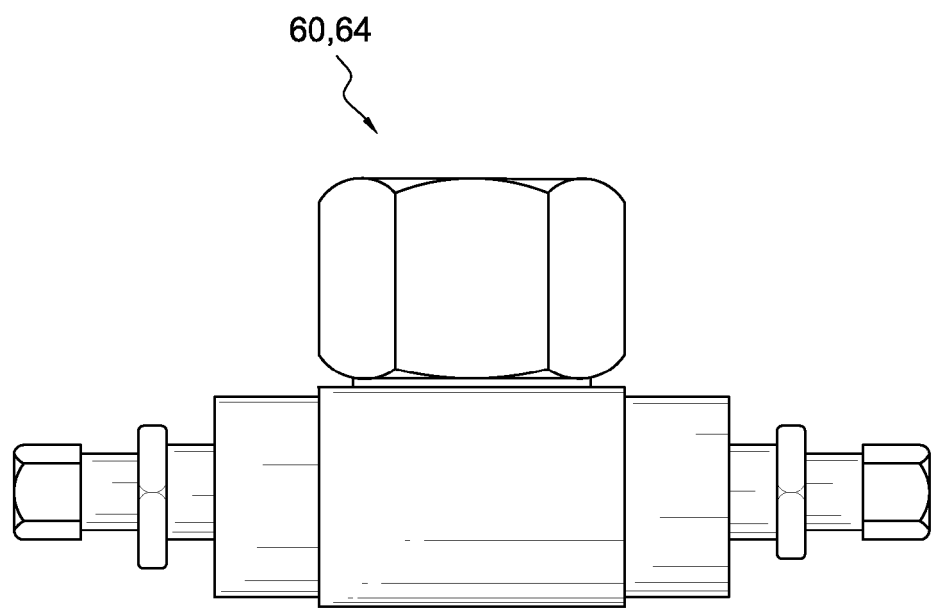
FIG. 5 is an elevational view of the valve of FIG. 4.
Figure 6:
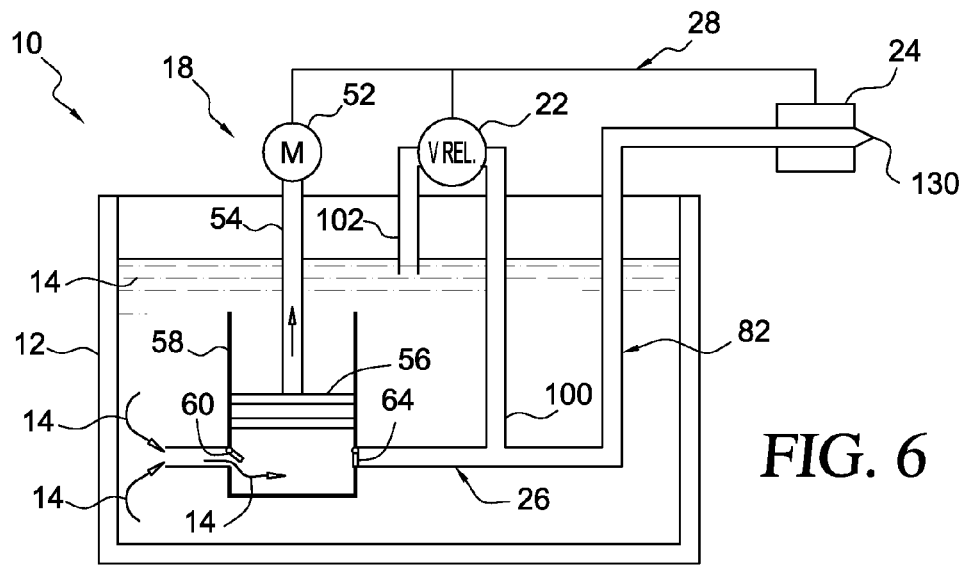
FIG. 6 is a schematic view of the system illustrated in FIG. 1 and showing the system as the bellows pulls cryogen within the cylinder.
Figure 7:
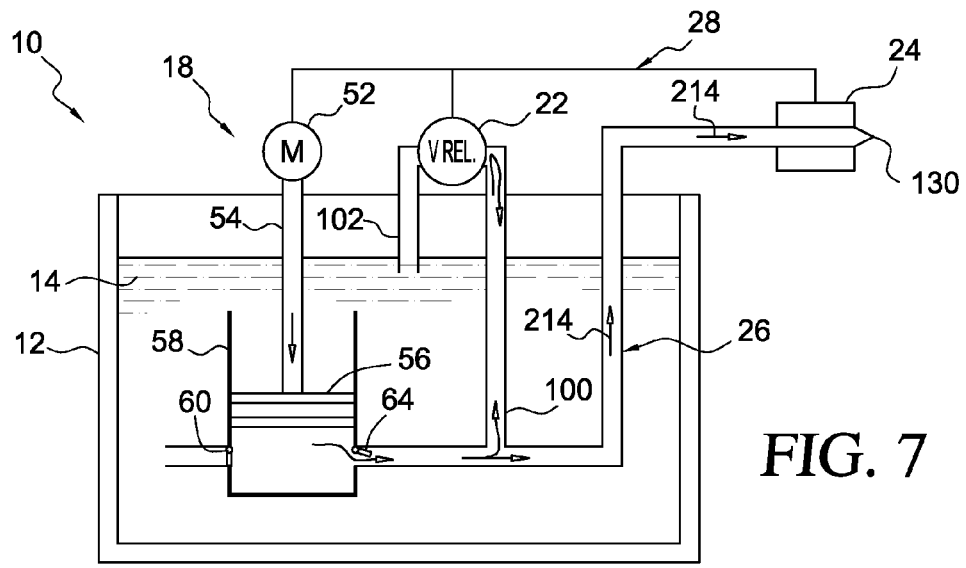
FIG. 7 is a schematic view similar to FIG. 6 but showing the system as the bellows initially pushes cryogen to the probe.
Figure 8:
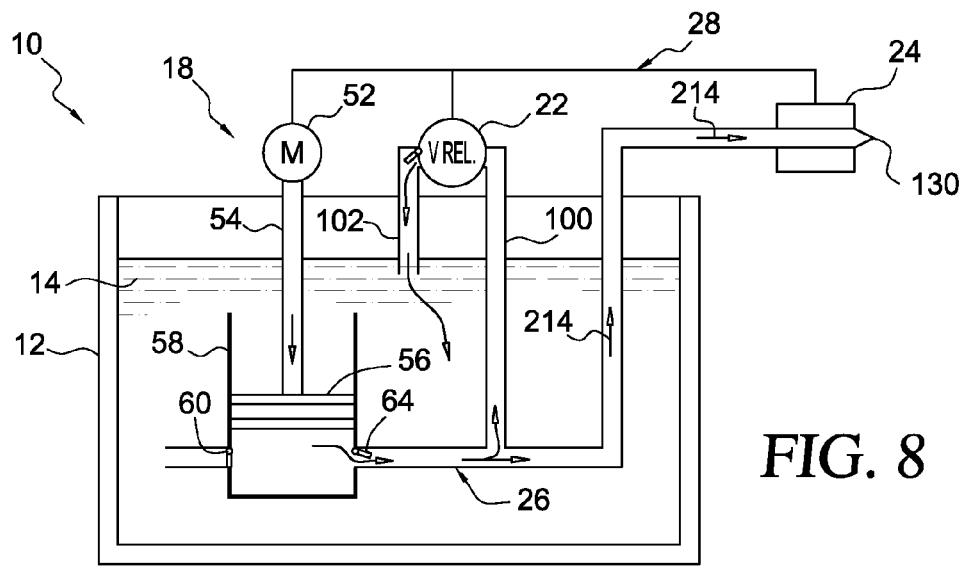
FIG. 8 is a schematic view similar to FIGS. 6 and 7 but showing the system as the bellows pushes cryogen to the probe and with the pressure relief valve activated to control the fluid pressure.

FIGS. 1-8 illustrate a preferred embodiment of a cryogenic pump, system, and method according to the present invention. The system 10 provides instantaneous sub-cooling of liquid cryogen 14, thereby creating a cryogen state characterized by an excess capacity to absorb heat without boiling. By manipulating the pressure relationships in the plumbing circuit 26, sub-cooled liquid 214 is transported to the distal cryoprobe tip 130 in 1-20 seconds allowing near instantaneous freezing at the probe tip 130. This rate of cooling is faster and the attainable low temperature is lower than comparable Joule-Thompson-based cryogenic devices.

The illustrated system 10 includes a container or dewar 12 containing cryogen 14, such as liquid nitrogen. A support 16 is positioned within the container 12 and submerged within the cryogen 14. A pump 18 is coupled to the container 12 such that the piston 56, illustrated in the form of a bellows, is also submerged within the cryogen 14. By way of a conduit system 26, the bellows 56 is fluidly coupled to an output manifold 20, a pressure release valve 22, and a surgical probe 24. A control system 28 monitors the temperature of the probe tip 130 and adjusts the system components as necessary to maintain the desired temperature at probe tip 130.

The container 12 is of substantially conventional design, except that it is appropriately adapted to support pump 18. Pump 18 includes a linear drive motor 52 mounted outside the container 12 and, preferably mounted to the top of the container 12. A drive shaft 54 extends down from the motor 52, through the cryogen 14 and couples to the bellows 56. The bellows 56 is appropriately constructed to fit within a cylinder 58. Bellows 56 is preferably formed from stainless steel. Also, although the figures illustrate a system 10 with two bellows 56, any appropriate number of bellow systems may be employed. The cylinder 58 has a one-way inlet valve 60 coupled to an inlet conduit 62, and a one-way outlet valve 64 coupled to an outlet conduit. The cylinder 58 and bellows 56 assembly is rigidly secured to the support 16 along with manifold 20.

Manifold 20 has an inlet conduit 80 fluidly coupled to the outlet valves 64 of the bellows 56. Manifold 20 also has outlet conduits 82 fluidly coupled to the probe 24. Although five outlet conduits 82 are illustrated it should be understood that the number of outlet conduits 82 is dependent on the system requirements, and that more or fewer outlet conduits 82 may be used. The manifold 20 also has an outlet port 84 for coupling with the pressure relief valve 22.

Pressure relief valve 22 is preferably mounted outside the container 12 and is coupled to the manifold by inlet conduit 100. The valve 22 also has an outlet conduit that leads back into the cryogen 14 in container 12 to return, to the container 12, the cryogen 14 that has been released from the conduit system 26 to lower the pressure as desired.

The surgical apparatus illustrated is shown as probe 24 with its corresponding tip 130 and is intended to represent any appropriate cryosurgical device, including probe tips, such as those known in the prior art. Examples of prior art probes are disclosed in the patents incorporated herein as set forth above.

Thus, the illustrated embodiment includes a reciprocating stainless steel bellows pump 18 that operates while submerged in liquid cryogen 14 and that causes instantaneous sub-cooling of the liquid cryogen 14 during the compression stroke of the bellows 56, thereby creating a cryogen state characterized by an excess capacity to absorb heat without boiling. Further, by manipulating the pressure relationships in the plumbing circuit 26, sub-cooled liquid 214 is transported to the distal cryoprobe tip 130 in 1-20 seconds allowing near instantaneous freezing at the probe tip 130.

In the illustrated embodiment, one or more stainless steel bellows "pistons" 56 are driven by a surface mounted linear drive system 52 capable of pressure regulation. The reciprocating action of each bellows piston 56 a) sequentially produces a negative pressure to draw in liquid cryogen 14 on the fill stroke through a one-way check valve 60 and b) sequentially discharge liquid cryogen 214 at a prescribed pressure profile out through a second one-way check valve 64 to a pressure manifold 20 connected to the probe 24 plumbing circuitry. The preferred, prescribed profile is a range of between 250 pounds per square inch (psi) and 400 pounds per square inch (psi).

The pressure pulse profile establishes an initial high, transient pressure spike that causes a colligative-based sub-cooling of the liquid cryogen 14, which establishes a boiling point differential of approximately 30-40 degrees Celsius, thereby establishing an excess temperature capacity (the level of temperature rise that can be allowed before boiling of the cryogen 14) supporting the instantaneous distribution of sub-cooled cryogen 214 in the plumbing circuit 26. Following the transient pressure spike, pressure is reduced to a base level to sustain the desired rate of ice growth a the distal end of the circuit, that is, at the probe 24. Conventional control system technology can be employed in controlling the interaction between the probe 24 and the pressure relief valve 22 and/or the pump 18, that is, in producing the control system 28.

Pressure relief and control is provided by an appropriately designed pressure transducer-valve interface 22 outside the cryogen-containing dewar 12.

Thus, while the invention has been disclosed and described with reference with a limited number of embodiments, it will be apparent that variations and modifications may be made thereto without departure from the spirit and scope of the invention and various other modifications may occur to those skilled in the art. Therefore, the following claims are intended to cover modifications, variations, and equivalents thereof.

The invention claimed is:

1. A cryosurgical system, comprising:
   a container having a cryogen within said container;
   at least one cryoprobe in fluid communication with said container;
   a pressure relief device in fluid communication with said container; and
   a pump assembly comprising:
      an elongated drive shaft;
      a piston coupled to said drive shaft, said piston being submerged within said cryogen within said container;
      a one-way inlet valve in fluid communication with said container; and
      a one-way outlet valve in fluid communication with said container.

2. A system according to claim 1, wherein said cryogen is liquid nitrogen.

3. A system according to claim 1, wherein said piston is a bellows.

4. A system according to claim 1, wherein the pressure relief device is-positioned between said pump and said cryoprobe.

5. A system according to claim 1, further comprising a supply manifold in fluid communication with said piston.

6. A system according to claim 5, wherein said supply manifold comprises a plurality of ports for connection to a plurality of cryoprobes.

7. A pump assembly for a cryosurgical system, comprising:
   a driving mechanism coupled to an elongated drive shaft;
   a piston coupled to said drive shaft and adapted to be submersed in a cryogen;
   a one-way inlet valve in fluid communication with said piston;
   a one-way outlet valve in fluid communication with said piston; and
   a supply manifold in fluid communication with said outlet valve, said supply manifold having at least one port for connection to a cryoprobe.

8. A pump assembly according to claim 7, wherein said supply manifold comprises a plurality of ports.

9. A pump assembly according to claim 7, wherein said piston is a bellows.

10. A pump assembly according to claim 7, wherein said cryogen is liquid nitrogen.

11. A method of delivering cryogen to a surgical device, comprising:
   providing a container having a cryogen within the container;
   providing a pump having a piston within a cylinder, said piston being submerged within the cryogen within said container;
   providing a one-way inlet valve in fluid communication with said piston;

providing a one-way outlet valve in fluid communication with said piston;

providing at least one surgical device outside the container for use in cryosurgical procedures;

providing at least one conduit fluidly interconnecting the container and the surgical device permitting the cryogen to flow from the container to the surgical device upon activation of the piston; and activating the piston to increase a pressure of the cryogen.

12. A method according to claim 11, wherein the step of activating the piston to increase the pressure of the cryogen comprises drawing the cryogen into the cylinder and discharging the cryogen from the cylinder to the surgical device.

13. A method according to claim 12, wherein cryogen is discharged to the surgical device at a predetermined pressure of between approximately 250 pounds per square inch and approximately 400 pounds per square inch.

14. A method according to claim 13, further comprising the step of activating a pressure release device to decrease the pressure of the cryogen to a pressure that is lower than the predetermined pressure after discharging the cryogen to the surgical device at the predetermined pressure.

15. A method according to claim 11, further including the step of providing a pressure relief device positioned between the piston and the surgical device.

16. A method according to claim 11, wherein said piston is a bellows.

17. A method according to claim 11, wherein said surgical device is a cryoprobe.

18. A method according to claim 11, wherein said cryogen is liquid nitrogen.

19. A cryosurgical system, comprising:
a container for receiving a cryogen within the container;
a supply manifold in fluid communication with the container;
at least one cryoprobe in fluid communication with the supply manifold and the container;
a pressure relief device in fluid communication with the container; and
a means for increasing a pressure of the cryogen for delivery to the supply manifold, wherein the means for increasing the pressure of the cryogen is independent of adding additional cryogen to the container.

20. A system according to claim 19, wherein the means for increasing a pressure of the cryogen in the container comprises increasing the pressure at a predetermined pressure of between approximately 250 pounds per square inch and approximately 400 pounds per square inch.

21. A method of delivering cryogen to a cryoprobe, comprising:
providing a container having a cryogen within the container;
providing at least one supply manifold;
providing at least one cryoprobe outside the container;
providing at least one conduit fluidly interconnecting the container, the supply manifold and the cryoprobe permitting the cryogen to flow from the container to the cryoprobe;
increasing a pressure of the cryogen for delivery to the supply manifold to a predetermined pressure, wherein the step of increasing the pressure of the cryogen is independent of adding additional cryogen to the container; and
activating a pressure relief device to decrease the pressure of the cryogen in the container to a pressure that is below the predetermined pressure.

* * * * *